(12) United States Patent
Balanev et al.

(10) Patent No.: US 9,351,753 B2
(45) Date of Patent: May 31, 2016

(54) ULTRASONIC MEDICAL INSTRUMENT WITH A CURVED WAVEGUIDE

(75) Inventors: Andrey Balanev, Saint-Petersburg (RU); Sergey Kvashnin, Moscow (RU); Georgy Martsinovskiy, Saint-Petersburg (RU); Igoris Misuchenko, Saint-Petersburg (RU); Alexey Ruin, Saint-Petersburg (RU)

(73) Assignee: Covidien LP, Mansfield, MA (US)

(*) Notice: Subject to any disclaimer, the term of this patent is extended or adjusted under 35 U.S.C. 154(b) by 736 days.

(21) Appl. No.: 13/360,910

(22) Filed: Jan. 30, 2012

(65) Prior Publication Data

US 2013/0197511 A1 Aug. 1, 2013

(51) Int. Cl.
*A61B 17/32* (2006.01)
*A61B 17/29* (2006.01)

(52) U.S. Cl.
CPC . *A61B 17/320092* (2013.01); *A61B 17/320068* (2013.01); *A61B 2017/2904* (2013.01); *A61B 2017/2929* (2013.01)

(58) Field of Classification Search
CPC ............... A61B 17/320068; A61B 17/320092; A61B 2017/2904; A61B 2017/2929; A61B 18/085
USPC .................................................... 606/27, 41
See application file for complete search history.

(56) References Cited

U.S. PATENT DOCUMENTS

| | | |
|---|---|---|
| 3,469,211 A | 9/1969 | Shoh et al. |
| 4,074,840 A * | 2/1978 | Fulenwider et al. ......... 225/96.5 |
| 4,277,710 A | 7/1981 | Harwood et al. |
| 4,587,958 A | 5/1986 | Noguchi et al. |
| 4,827,911 A | 5/1989 | Broadwin et al. |
| 4,922,902 A | 5/1990 | Wuchinich et al. |
| 4,965,532 A | 10/1990 | Sakurai |
| 4,973,876 A | 11/1990 | Roberts |
| 4,974,581 A | 12/1990 | Wiksell |
| 5,180,363 A | 1/1993 | Idemoto et al. |
| 5,216,338 A | 6/1993 | Wilson |
| 5,330,502 A | 7/1994 | Hassler et al. |
| 5,421,829 A | 6/1995 | Olichney et al. |
| 5,456,684 A | 10/1995 | Schmidt et al. |
| 5,532,539 A | 7/1996 | Hielscher |
| 5,562,682 A | 10/1996 | Oberlin et al. |
| 5,634,466 A | 6/1997 | Gruner |

(Continued)

FOREIGN PATENT DOCUMENTS

| | | |
|---|---|---|
| AU | 200179486 B2 | 5/2002 |
| CA | 2 359 403 A1 | 4/2002 |

(Continued)

*Primary Examiner* — Christopher A Flory (57) ABSTRACT

A forceps includes a housing, a curved waveguide, one or more movable members, and an end effector assembly. The housing includes one or more transducers configured to generate a mechanical vibration in response to energy transmitted thereto from an energy source. The curved waveguide extends from the housing and is configured to receive the mechanical vibration generated by the one or more transducers. The one or more movable members are positioned along the curved waveguide. The one or more movable members are configured to translate mechanical movement from the housing to the end effector assembly. The end effector assembly is disposed at a distal end of the curved waveguide and includes a movable jaw member pivotable between approximated and unapproximated positions relative to a distal end of the curved waveguide in response to movement of the one or more movable members.

20 Claims, 5 Drawing Sheets

(56) References Cited

U.S. PATENT DOCUMENTS

| | | | |
|---|---|---|---|
| 5,637,947 A | 6/1997 | Kising et al. | |
| 5,649,957 A | 7/1997 | Levin | |
| 5,700,952 A | 12/1997 | Andersen | |
| 5,702,408 A | 12/1997 | Wales et al. | |
| 5,704,534 A | 1/1998 | Huitema et al. | |
| 5,707,369 A | 1/1998 | Vaitekunas et al. | |
| 5,797,537 A | 8/1998 | Oberlin et al. | |
| 5,816,476 A | 10/1998 | Buice et al. | |
| 5,817,119 A | 10/1998 | Klieman et al. | |
| 5,873,873 A * | 2/1999 | Smith et al. | 606/1 |
| 5,897,523 A | 4/1999 | Wright et al. | |
| 6,063,098 A | 5/2000 | Houser et al. | |
| 6,163,100 A | 12/2000 | Morizaki et al. | |
| 6,241,139 B1 | 6/2001 | Milliman et al. | |
| 6,243,525 B1 * | 6/2001 | Luizink et al. | 385/132 |
| 6,320,298 B1 | 11/2001 | Kawabe | |
| 6,454,782 B1 | 9/2002 | Schwemberger et al. | |
| 6,480,796 B2 | 11/2002 | Wiener | |
| 6,569,109 B2 | 5/2003 | Sakurai et al. | |
| 6,588,277 B2 | 7/2003 | Giordano et al. | |
| 6,626,926 B2 | 9/2003 | Friedman et al. | |
| 6,652,547 B2 | 11/2003 | Rabiner et al. | |
| 6,663,641 B1 | 12/2003 | Kovac et al. | |
| 6,666,854 B1 | 12/2003 | Lange | |
| 6,678,621 B2 | 1/2004 | Wiener et al. | |
| 6,679,899 B2 | 1/2004 | Wiener et al. | |
| 6,752,815 B2 | 6/2004 | Beaupre | |
| 6,761,690 B2 | 7/2004 | Sakurai et al. | |
| 6,773,444 B2 | 8/2004 | Messerly | |
| 6,898,536 B2 | 5/2005 | Wiener et al. | |
| 6,984,919 B2 | 1/2006 | Iino et al. | |
| 7,179,271 B2 | 2/2007 | Friedman et al. | |
| 7,247,141 B2 | 7/2007 | Makin et al. | |
| 7,270,646 B2 | 9/2007 | Sakurai et al. | |
| 7,273,483 B2 | 9/2007 | Wiener et al. | |
| 7,475,801 B2 | 1/2009 | Johansen et al. | |
| 7,481,824 B2 | 1/2009 | Boudreaux et al. | |
| 7,482,888 B1 | 1/2009 | Kleveland | |
| 7,503,895 B2 | 3/2009 | Rabiner et al. | |
| 7,513,160 B2 | 4/2009 | Lynch et al. | |
| 7,514,844 B2 | 4/2009 | Unkrich | |
| 7,528,670 B2 | 5/2009 | Soh | |
| 7,566,334 B2 | 7/2009 | Christian et al. | |
| 7,614,878 B2 | 11/2009 | Paschke et al. | |
| 7,963,964 B2 * | 6/2011 | Santilli | A61B 18/1442 606/205 |
| 8,475,453 B2 * | 7/2013 | Marczyk | A61B 18/1445 606/51 |
| 8,479,969 B2 * | 7/2013 | Shelton, IV | 227/180.1 |
| 8,662,745 B2 * | 3/2014 | Misuchenko et al. | 374/1 |
| 2002/0052595 A1 * | 5/2002 | Witt | A61B 17/320092 606/1 |
| 2002/0091404 A1 | 7/2002 | Beaupre | |
| 2002/0128674 A1 | 9/2002 | Beaupre | |
| 2003/0083683 A1 | 5/2003 | Schwemberger et al. | |
| 2005/0027311 A1 | 2/2005 | Wiener et al. | |
| 2005/0070800 A1 | 3/2005 | Takahashi | |
| 2005/0216045 A1 * | 9/2005 | Young et al. | 606/169 |
| 2006/0020262 A1 * | 1/2006 | Witt et al. | 606/40 |
| 2007/0112306 A1 | 5/2007 | Agnew | |
| 2008/0234711 A1 | 9/2008 | Houser et al. | |
| 2008/0277447 A1 | 11/2008 | Smith et al. | |
| 2008/0294191 A1 | 11/2008 | Lee | |
| 2008/0308607 A1 | 12/2008 | Timm et al. | |
| 2008/0319442 A1 * | 12/2008 | Unger | A61B 18/1445 606/48 |
| 2009/0036913 A1 | 2/2009 | Wiener et al. | |
| 2009/0036914 A1 | 2/2009 | Houser | |
| 2009/0065549 A1 | 3/2009 | Viola | |
| 2009/0069842 A1 | 3/2009 | Lee et al. | |
| 2009/0076534 A1 | 3/2009 | Shelton, IV et al. | |
| 2009/0118751 A1 | 5/2009 | Wiener et al. | |
| 2009/0131962 A2 | 5/2009 | Houser et al. | |
| 2009/0143797 A1 | 6/2009 | Smith et al. | |
| 2009/0163836 A1 | 6/2009 | Sliwa | |
| 2009/0187185 A1 | 7/2009 | Lyons et al. | |
| 2009/0198272 A1 | 8/2009 | Kerver et al. | |
| 2009/0275864 A1 * | 11/2009 | Hirai | 601/2 |
| 2010/0030248 A1 * | 2/2010 | Palmer et al. | 606/169 |
| 2010/0041945 A1 * | 2/2010 | Isbell, Jr. | A61B 17/29 600/104 |
| 2010/0057121 A1 * | 3/2010 | Piskun | A61B 17/29 606/206 |
| 2010/0087758 A1 | 4/2010 | Beaupre et al. | |
| 2010/0204721 A1 | 8/2010 | Young et al. | |
| 2010/0331742 A1 * | 12/2010 | Masuda | 601/2 |
| 2011/0046522 A1 | 2/2011 | Chan et al. | |
| 2011/0295270 A1 * | 12/2011 | Giordano et al. | 606/130 |
| 2012/0078278 A1 * | 3/2012 | Bales et al. | 606/169 |
| 2012/0172904 A1 * | 7/2012 | Muir et al. | 606/169 |
| 2013/0197511 A1 * | 8/2013 | Balanev et al. | 606/41 |
| 2013/0281989 A1 * | 10/2013 | Isbell, Jr. | A61B 17/29 606/1 |
| 2014/0155921 A1 * | 6/2014 | Price et al. | 606/169 |
| 2014/0171966 A1 * | 6/2014 | Giordano et al. | 606/130 |
| 2014/0249574 A1 * | 9/2014 | Piskun | A61B 17/29 606/206 |
| 2015/0157354 A1 * | 6/2015 | Bales et al. | A61B 17/320068 |
| 2015/0327852 A1 * | 11/2015 | Isbell, Jr. | A61B 17/29 227/175.2 |

FOREIGN PATENT DOCUMENTS

| | | |
|---|---|---|
| EP | 0 908 155 | 4/1999 |
| EP | 1 199 046 B1 | 4/2002 |
| EP | 1 201 196 B1 | 3/2006 |
| EP | 2 000 106 A1 | 12/2008 |
| JP | 2000-237204 A | 9/2000 |
| WO | WO 02/062241 A1 | 8/2002 |

* cited by examiner

ULTRASONIC MEDICAL INSTRUMENT WITH A CURVED WAVEGUIDE

BACKGROUND

1. Technical Field

The present disclosure relates to surgical instruments and, more particularly, to an endoscopic forceps that utilizes ultrasound to treat and cut tissue.

2. Background of Related Art

As an alternative to open instruments for use with open surgical procedures, many modern surgeons use endoscopes and endoscopic electrosurgical apparatuses (e.g., endoscopic or laparoscopic forceps) for remotely accessing organs through smaller, puncture-like incisions. These instruments are particularly suited for use in minimally invasive procedures, such as endoscopic or laparoscopic procedures where patients tend to benefit from less scarring, less pain, and reduced healing time. Typically, the endoscopic forceps is inserted into the patient through one or more various types of cannulas or access ports (typically having an opening that ranges from about five millimeters to about fifteen millimeters) that has been made with a trocar; as can be appreciated, smaller cannulas are usually preferred.

Some endoscopic instruments may utilize ultrasound vibrations to effectuate certain medical procedures. In particular, ultrasonic instruments utilize mechanical vibration energy transmitted at ultrasonic frequencies to treat tissue. When transmitted at suitable energy levels, ultrasonic vibrations may be used to coagulate, cauterize, fuse, cut, desiccate, and/or fulgurate tissue to effect hemostasis.

An endoscopic forceps that utilizes ultrasound and is configured for use with small cannulas (e.g., cannulas less than five millimeters) may present design challenges for a manufacturer of endoscopic instruments.

SUMMARY

One aspect of the present disclosure includes a forceps includes a housing, a curved waveguide, one or more movable members, and an end effector assembly. The housing has one or more transducers configured to generate a mechanical vibration in response to energy transmitted thereto from an energy source. The mechanical vibration may have an ultrasonic frequency.

In another aspect of the present disclosure, the curved waveguide extends from the housing and is configured to receive the mechanical vibration generated by the one or more transducers. The curved waveguide includes linear and curvilinear sections. The curved waveguide may have two or more radii of curvature disposed in opposing relationship relative to one another such that the curved waveguide curves towards and away from a longitudinal axis defined through the forceps.

In one aspect of the present disclosure, the one or more movable members are positioned along the curved waveguide and configured to translate mechanical movement from the housing to the end effector assembly. The one or more movable members may move relative to the curved waveguide independently of the curved waveguide or may move a movable jaw member relative to the distal end of the curved waveguide. The one or more movable members may include a spiral configuration and move axially along the curved waveguide and/or rotatably about the curved waveguide independently of the curved waveguide.

In one aspect of the present disclosure, the end effector assembly is disposed at a distal end of the curved waveguide and includes a movable jaw member pivotable between approximated and unapproximated positions relative to a distal end of the curved waveguide in response to movement of the one or more movable members. The movable jaw member may be rotatable around the distal end of the curved waveguide. The end effector assembly may include a second jaw member. The distal end of the curved waveguide may act as the second jaw member.

In yet another aspect of the present disclosure, the forceps includes a trigger assembly operably coupled to the housing that includes an activation trigger and a clamping trigger. The activation trigger is configured to facilitate the transmission of the energy from the energy source to the one or more transducers upon the actuation of the activation trigger. The clamping trigger is configured to move the one or more movable members upon the actuation of the clamping trigger in order to pivot the movable jaw member between the approximated and unapproximated positions.

In still another aspect of the present disclosure, the forceps may include a rotating assembly operably coupled to the housing and configured to move the one or more movable members upon rotation of the rotating assembly in order to rotate the movable jaw member around the distal end of the curved waveguide.

In one aspect of the present disclosure, the forceps may include a battery that acts as the energy source. The battery may be a smart battery. The forceps may include a battery that acts as an energy source operatively coupled to the one or more transducers.

In another aspect of the present disclosure, a forceps includes a housing, a curved waveguide, and one or more movable members. The housing includes one or more transducers configured to generate a mechanical vibration.

In one aspect of the present disclosure, the movable members may extend from the housing and are operatively coupled to a movable jaw member. The movable members are movable around and/or along the length of the curved waveguide to pivot the movable jaw member relative to a distal end of the curved waveguide. The movable members may move axially along the curved waveguide and/or rotatably about the waveguide independently of the curved waveguide to pivot the movable jaw member relative to the distal end of the curved waveguide. The movable members may have a spiral configuration.

In one aspect of the present disclosure, the forceps may include an immovable jaw member disposed adjacent the movable jaw.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION OF THE EMBODIMENTS

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end which is closer to the user, while the term "distal" will refer to an end that is farther from the user.

Figure 1:
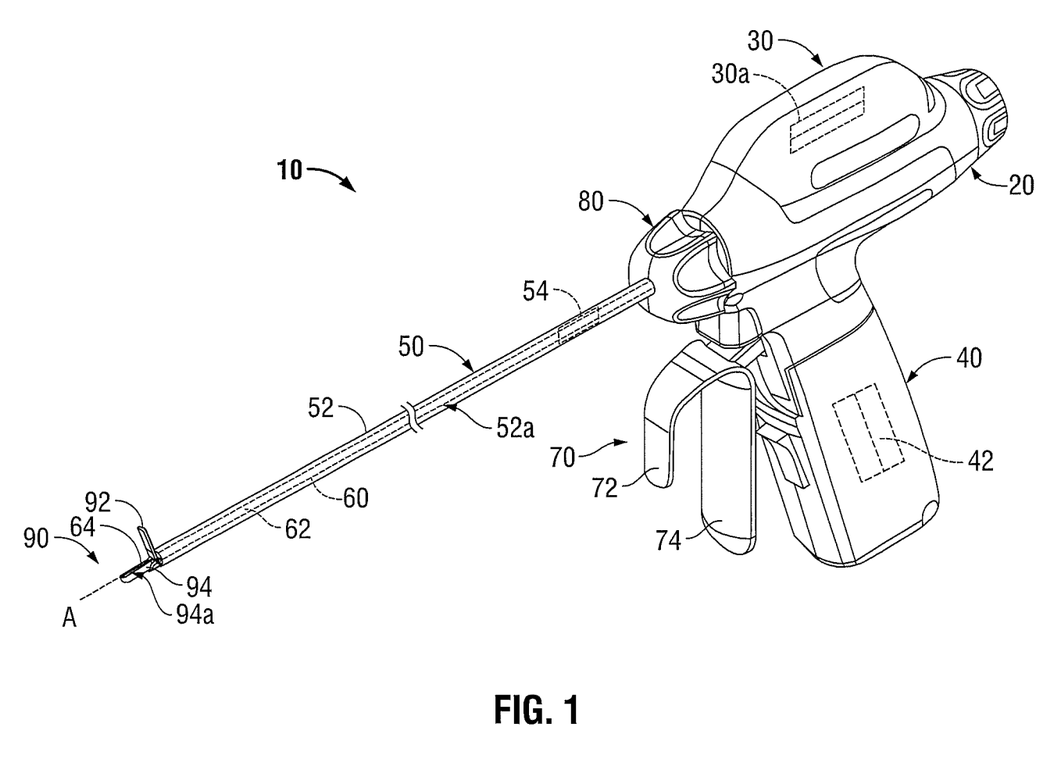
FIG. 1 shows a perspective view of one example of an ultrasonic instrument.

With initial reference to FIG. 1, an embodiment of an ultrasonic instrument 10 (e.g., a forceps) is shown for use with various surgical procedures and generally includes a housing 20, a transducer assembly 30, an energy assembly 40, a shaft assembly 50, a waveguide assembly 60, a trigger assembly 70, a rotating assembly 80, and an end effector assembly 90 that mutually cooperate to grasp, treat, and divide tubular vessels and vascular tissue.

Figure 2:
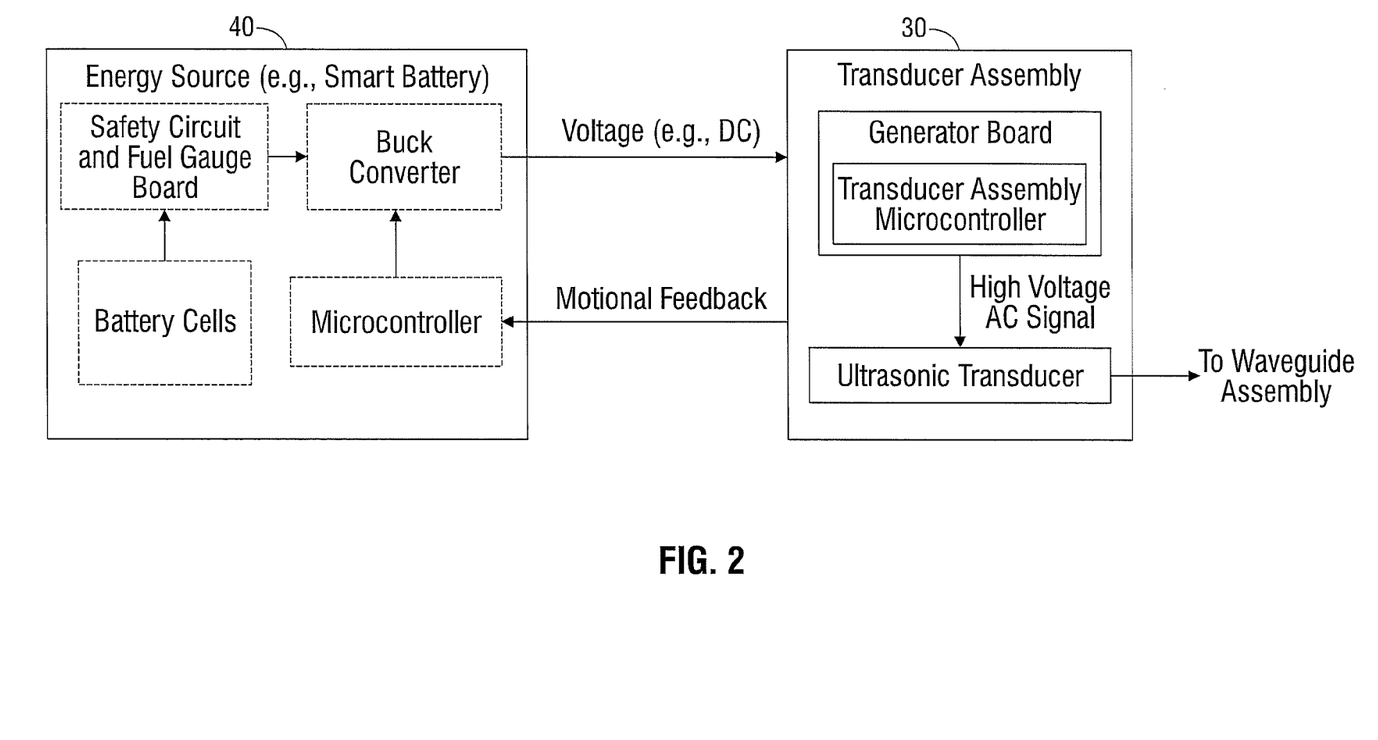
FIG. 2 is a block diagram depicting the interaction between an energy source and a transducer assembly of the ultrasonic instrument of FIG. 1.

Ultrasonic instrument 10 is powered by the energy assembly 40 when the energy assembly 40 is operably connected to the ultrasonic instrument 10. The energy assembly 40 may include one or more batteries 42 and/or one or more electrosurgical cables (not shown) to transfer energy, e.g. voltage from DC and/or AC signals, to the ultrasonic instrument 10. The ultrasonic instrument 10 may include a smart battery that controls the charge and discharge of its battery cells and communicates with the transducer assembly 30 as illustrated in FIG. 2.

In embodiments with one or more electrosurgical cables, the ultrasonic instrument 10 is connectable to an external source of energy, e.g., any suitable generator (not shown) known in the art.

Figure 3:
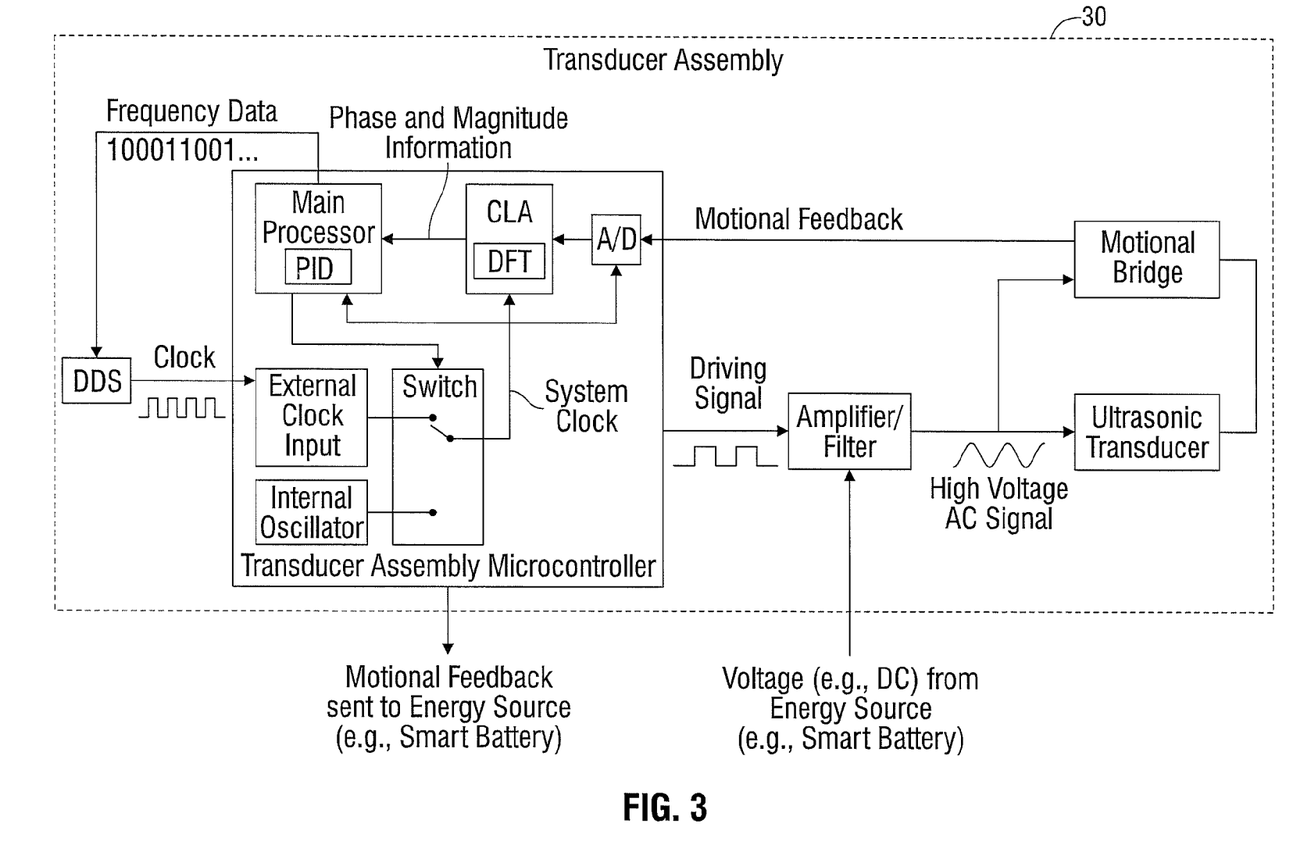
FIG. 3 is a block diagram depicting the transducer assembly of FIG. 2.

The transducer assembly 30 includes one or more ultrasonic transducers 30a operably coupled to the housing 20. Each transducer, which may be positioned within the housing 20, converts the energy transmitted thereto from the energy assembly 40 into high frequency mechanical motion, e.g., ultrasonic vibration. As such, the frequency of the ultrasonic vibration in the one or more transducers is controlled by the frequency of the energy signal, e.g., high voltage AC signal, applied to the one or more transducers. As depicted in FIG. 3, this frequency control may be accomplished by a phase-lock loop in the transducer assembly 30.

With reference to FIG. 1, the shaft assembly 50, which may be at least partially disposable, includes a shaft 52 which extends from the housing 20 and defines a central lumen 52a therethrough. The central lumen 52a receives at least a portion of the waveguide assembly 60 and a drive assembly 54 therein. The drive assembly 54 is operably coupled to the trigger assembly 70 at a proximal end of the drive assembly 54 and is operably coupled to the end effector assembly 90 at a distal end of the drive assembly 54 for operating the end effector assembly 90 upon the actuation of the trigger assembly 70.

The end effector assembly 90, which may be at least partially disposable, includes a pair of opposing jaw members 92, 94. The first jaw member 92 pivots relative to the second jaw member 94 via the drive assembly 54 upon the actuation of the trigger assembly 70, positioning jaw members 92, 94 between approximated (closed) and unapproximated (open) configurations. Second jaw member 94 defines a channel 94a therethrough. Second jaw member 94 may be immovable.

With continued reference to FIG. 1, the waveguide assembly 60 is positioned within the shaft 52 of the shaft assembly 50 and is configured to receive and transmit the ultrasonic mechanical vibration generated by the one or more transducers. The waveguide assembly 60 includes a waveguide 62 and an ultrasonic treatment member 64 operably coupled to the distal end of the waveguide 62. The waveguide assembly 60 is at least partially positionable within one or both jaw members 92, 94 of the end effector assembly 90. More particularly, at least a portion of the ultrasonic treatment member 64 is positionable within the channel 94a defined by jaw member 94 of the end effector assembly 90. The ultrasonic treatment member 64 is configured to receive the mechanical vibration from the one or more transducers and transmit the mechanical vibration to treat tissue positioned within end effector assembly 90. The waveguide assembly 60 may be longitudinally translatable with respect to the end effector assembly 90.

The rotating assembly 80 is operatively connected to the housing 20 and is rotatable in either direction about the longitudinal axis of the shaft assembly 50 to rotate the shaft assembly 50 and the end effector assembly 90 about the longitudinal axis "A" of the shaft assembly 50. This enables the user to position and re-position the ultrasonic instrument 10 prior to activation and sealing. The rotating assembly 80 is operably coupled to the shaft assembly 50. A more detailed description of rotating assembly 80 is described in U.S. Pat. No. 7,101,371, entitled "VESSEL SEALER AND DIVIDER" by Dycus et al., the entire contents of which are incorporated herein by this reference.

The trigger assembly 70 includes an activation trigger 72 for activating energy from the energy assembly 40 and a clamping trigger 74 for operating the end effector assembly 90. The trigger assembly 70 is operably coupled to the housing 20. The activation trigger 72 is configured to facilitate the transmission of the energy from the energy source 42 to the one or more transducers upon the actuation thereof. The clamping trigger 74 is configured to move the drive assembly 54 in order to move the opposing jaw members 92, 94 between unapproximated and approximated configurations upon the actuation of the clamping trigger 74. In this manner, the clamping trigger 74 of the trigger assembly 70 is operatively connected to the shaft assembly 50 to impart movement to first and second jaw members 92, 94 from an unapproximated (open) position, where the jaw members 92, 94 are in spaced relation relative to one another, to a clamping or approximated (closed) position, where the jaw members 92, 94 cooperate to grasp tissue therebetween.

In use, when the activation trigger 72 is actuated, the energy assembly 40 applies energy, e.g., the high voltage AC signal, to the transducer assembly 30. The activation trigger 72 may be configured to operate the ultrasonic instrument 10 in multiple modes of operation, including, but not limited to a low-power mode of operation and a high-power mode of operation. As discussed above, the energy is then converted by the transducer assembly 30 and transmitted from the transducer assembly 30 along the waveguide assembly 60 to the end effector assembly 90 in order to treat tissue grasped between the first and second jaws 92, 94 with ultrasonic vibrations.

Figure 4:
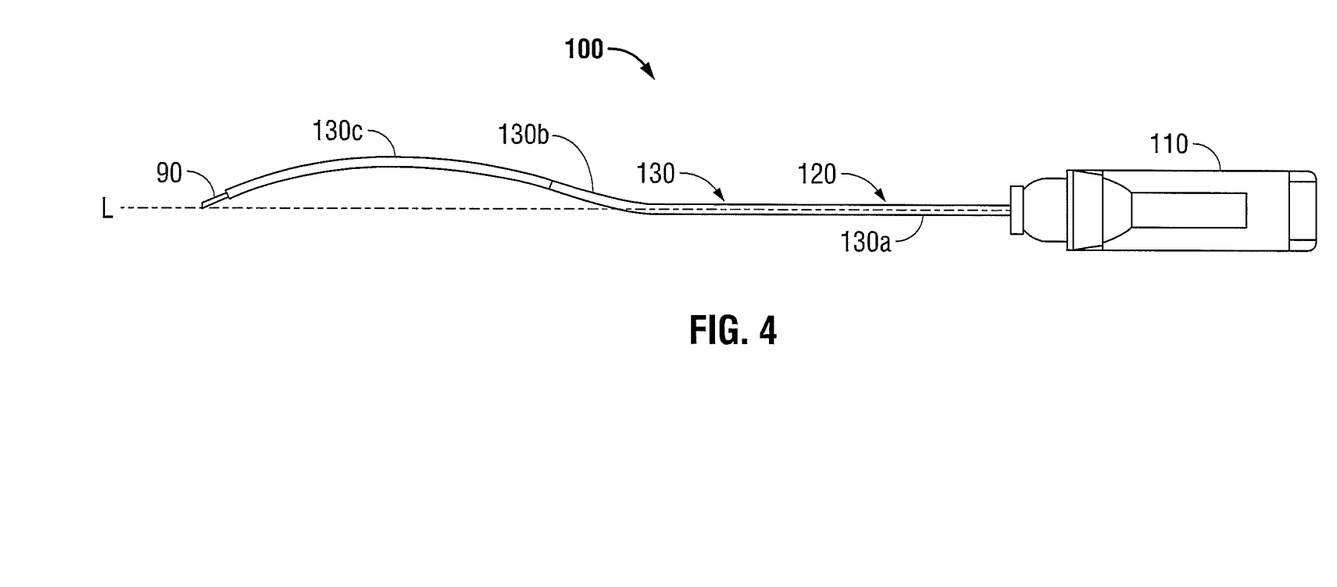
FIG. 4 shows a top view of one embodiment of an ultrasonic instrument in accordance with the principles of the present disclosure.

One embodiment of an ultrasonic instrument, generally referred to as 100, is depicted in FIG. 4. Ultrasonic instrument 100 is similar to ultrasonic instrument 10 and is described herein only to the extent necessary to describe the differences in construction and operation thereof. In particular, ultrasonic instrument 100 includes a housing assembly 110 having a shaft assembly 120 extending therefrom, an end effector assembly 90 operably coupled to a distal end of the shaft assembly 120. Shaft assembly 120 defines a longitudinal axis L extending therethrough. Shaft assembly 120 includes a curved waveguide 130 which may be formed of any suitable titanium alloy (e.g., ATI Ti-6AL-4V (UNS 56400)) or any other suitable material known in the art.

With continued reference to FIG. 4, curved waveguide 130 includes a first section 130a, a second section 130b, and a third section 130c. Waveguide 130 is curvilinear such that one or more of first section 130a, second section 130b, and third section 130c may be linear and/or curvilinear. For example, as depicted in FIG. 4, first section 130a is linear, second section 130b is partially linear and partially curvilinear, and third section 130c is curvilinear. As can be appreciated, one or more sections of waveguide 130 may have any suitable radius of curvature and may be curved relative to the longitudinal axis L at any suitable orientation about the circumference of the longitudinal axis L. As depicted in FIG. 4, second and third sections 130b, 130c curve laterally relative to the longitudinal axis L. In particular, second section 130b curves laterally away from longitudinal axis L while third section 130c curves partially laterally away from longitudinal axis L and partially laterally toward longitudinal axis L. Waveguide 130 may have any suitable cross-sectional shape and/or dimension. Further, waveguide 130 may have multiple cross-sectional shapes and/or dimensions along the length, of or a portion of the length, of waveguide 130. It should also be noted that waveguide 130 may be monolithically formed or have portions separately formed.

Figure 5:
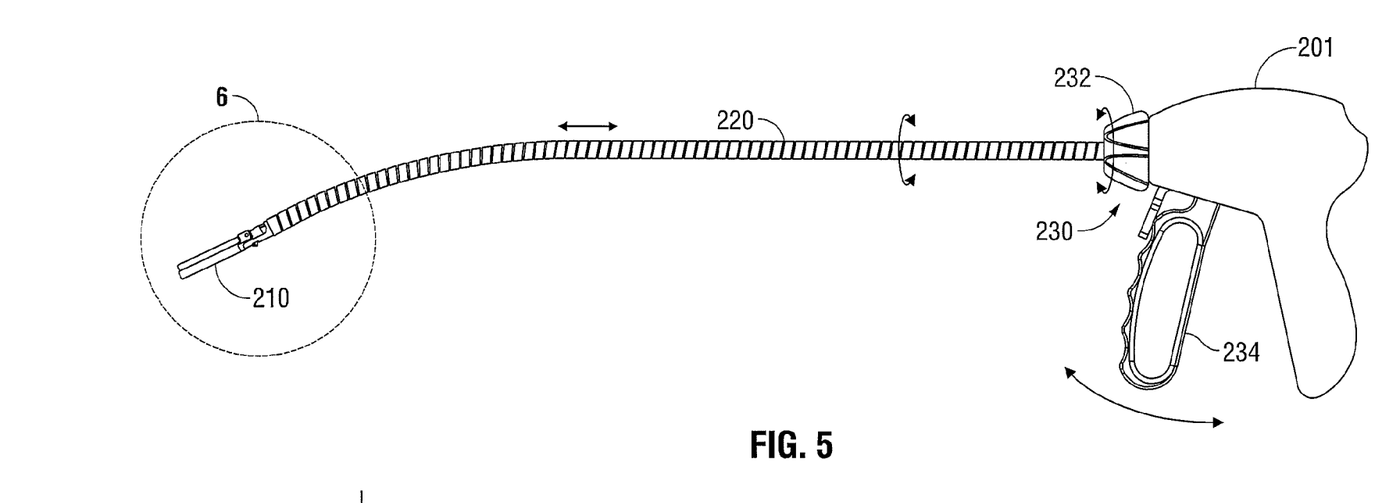
FIG. 5 is a perspective view of another embodiment of an ultrasonic instrument with jaw members thereof being shown in a closed configuration.
Figure 6:
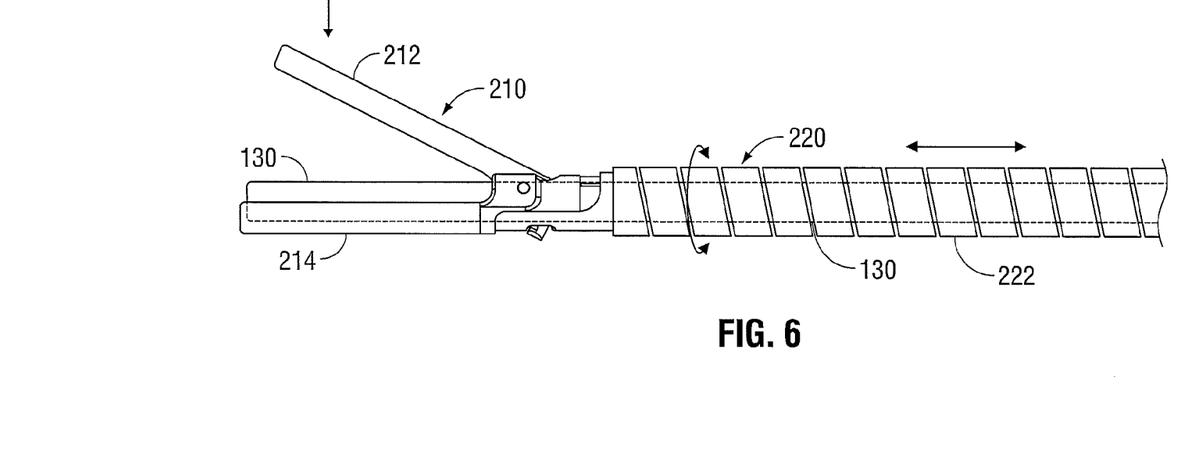
FIG. 6 is an enlarged perspective view of a distal end of the embodiment of the ultrasonic instrument depicted in FIG. 5 with the jaw members thereof shown in an open configuration.

Turning now to FIGS. 5-6, another embodiment of an ultrasonic instrument is shown which is generally referred to as ultrasonic instrument 200. Ultrasonic instrument 200 is similar to ultrasonic instrument 100 and is described herein only to the extent necessary to describe the differences in construction and operation thereof. In particular, ultrasonic instrument 110 includes a housing assembly 201, a trigger assembly 230, an end effector assembly 210, and a shaft assembly 220.

As best depicted in FIG. 6 shaft assembly 220 includes a movable member 222 and a curved waveguide 130 disposed within movable member 222. Some embodiments of movable member 222 include any suitable spiral member, spring, and/or flexible sheath as can be appreciated by one skilled in the art. Curved waveguide 130 may be axially and/or rotationally fixed relative to housing assembly 201 and/or movable member 222. End effector assembly 210 includes a first jaw member 212 and a second jaw member 214, each of which may be movable and/or immovable. Curved waveguide 130 may extend into one or both of first and second jaw members 212, 214 to treat tissue disposed between the first and second jaw member 212, 214 as discussed above with respect to waveguide assembly 60. Movable member 222 is secured to one or both of first and second jaw members 212, 214 at a distal end of movable member 222. Moveable member 222 may bias one or both of the first and second jaw members 212, 214 in an open and/or closed configuration. At a proximal end of movable member 222, movable member 222 is secured to housing assembly 201. Trigger assembly 230 is operatively coupled to housing assembly 201. Actuation of trigger assembly 230 moves movable member 222 about curved waveguide 130. Trigger assembly 230 may include knobs 232 and/or levers 234 and/or any other suitable device may be used to effectuate axial or rotational movement of movable member 222. Alternatively, trigger assembly 230, or components thereof, may be used to effectuate axial and rotational movement of movable member 222 (e.g., spiraling and/or spiral movement as illustrated by axial and rotational arrows in FIG. 6). To this end, movable member 222 may be moved (e.g., spiraled) about curved waveguide 130, independent of curved waveguide 130, to move one or both of first and second jaw members 212, 214 between open (unapproximated) and closed (approximated) positions. As can be appreciated, knobs 232 and/or levers 234 of trigger assembly 230 may be configured to generate mechanical vibrations through curved waveguide 130 as discussed above.

Further, in certain embodiments, second jaw member 214 of end effector assembly 210 may be eliminated. More specifically, a distal end of curved waveguide 130 may act as an immovable jaw member. In this respect, first jaw member 212 moves between approximated and unapproximated positions relative to the distal end of curved waveguide 130 (e.g., the portion of curved waveguide 130 acting as the immovable jaw member) in response to movement of movable member 222.

With this purpose in mind, the presently disclosed ultrasonic instruments may include any suitable number of electrical connections, configurations, and/or components (e.g., resistors, capacitors, inductors, rheostats, etc.), mechanical connections, configurations, and/or components (e.g., gears, links, springs, members, etc.), and/or electro-mechanical connections, configurations, and/or components such that presently disclosed ultrasonic instrument 10, 100 may function as intended. For example, one or both of the jaw members may be configured to seal tissue upon actuation of the instrument. With this in mind, one or both jaw members may include one or more stop members (or other mechanisms) to control the gap distance between active surfaces within a particular range of about 0.001 inches to about 0.006 inches. The handle or actuator may also be configured to exert a predetermined pressure on the tissue between about 3 kg/cm^2 to about 16 kg/cm^2. The ultrasonic generator may also need to be regulated to control the sealing angle.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A forceps, comprising:
    a housing having at least one transducer configured to generate a mechanical vibration;
    a curved waveguide extending from the housing to a distal end of the curved waveguide, the curved waveguide being monolithically formed and configured to receive the mechanical vibration generated by the at least one transducer;
    at least one movable member positioned along the curved waveguide, the at least one movable member being spirally movable relative to the curved waveguide; and
    an end effector assembly disposed at the distal end of the curved waveguide and including a movable jaw member pivotable between approximated and unapproximated positions relative to the distal end of the curved waveguide in response to spiral movement of the at least one movable member along a length of the curved waveguide.

2. The forceps according to claim 1, wherein the movable jaw member is rotatable around the distal end of the curved waveguide.

3. The forceps according to claim 1, wherein the at least one movable member moves relative to the curved waveguide independent of the curved waveguide to move the movable jaw member relative to the distal end of the curved waveguide.

4. The forceps according to claim 1, wherein the at least one movable member includes a spiral configuration and moves independent of the curved waveguide as the at least one movable member spirals about the curved waveguide.

5. The forceps according to claim 1, wherein the curved waveguide includes linear and curvilinear sections.

6. The forceps according to claim 5, wherein the curved waveguide has at least two radii of curvature.

7. The forceps according to claim 6, wherein the at least two radii of curvature are disposed in opposing relationship relative to one another such that the curved waveguide curves towards and away from a longitudinal axis defined through the forceps.

8. The forceps according to claim 1, wherein the mechanical vibration has an ultrasonic frequency.

9. The forceps according to claim 1, wherein the forceps includes a battery operably coupled to the at least one transducer.

10. The forceps according to claim 9, wherein the battery is a smart battery.

11. The forceps according to claim 1, further comprising a trigger assembly operably coupled to the housing, the trigger assembly including an activation trigger and a clamping trigger, the activation trigger configured to facilitate transmission of energy to the at least one transducer upon actuation of the activation trigger, the clamping trigger configured to move the at least one movable member upon actuation of the clamping trigger in order to pivot the movable jaw member between the approximated and unapproximated positions.

12. The forceps according to claim 11, further comprising a rotating assembly operably coupled to the housing, the rotating assembly configured to move the at least one movable member upon rotation of the rotating assembly in order to rotate the movable jaw member around the distal end of the curved waveguide.

13. The forceps according to claim 1, wherein the end effector assembly includes a second jaw.

14. The forceps according to claim 13, wherein the distal end of the curved waveguide acts as the second jaw.

15. A forceps, comprising:
a housing having at least one transducer configured to generate a mechanical vibration;
a movable jaw member;
a curved waveguide defining a length and having a distal end, the curved waveguide configured to receive the mechanical vibration generated by the at least one transducer; and
at least one movable member extending from the housing and being operatively coupled to the movable jaw member, the at least one movable member configured to spiral around and along the length of the curved waveguide to pivot the movable jaw member relative to the distal end of the curved waveguide.

16. The forceps according to claim 15, wherein the at least one movable member spirals about the curved waveguide independent of the curved waveguide to pivot the movable jaw member relative to the distal end of the curved waveguide.

17. The forceps according to claim 15, wherein the at least one movable member has a spiral configuration.

18. The forceps according to claim 15, wherein the curved waveguide includes linear and curvilinear sections.

19. The forceps according to claim 18, wherein the curved waveguide has at least two radii of curvature.

20. The forceps according to claim 15, further comprising an immovable jaw member disposed adjacent the movable jaw member.

* * * * *